(12) United States Patent
Sattig et al.

(10) Patent No.: US 7,959,349 B2
(45) Date of Patent: Jun. 14, 2011

(54) MIXING AND APPLICATION DEVICE

(75) Inventors: Christoph Sattig, Dieburg (DE); Volker Stirnal, Dieburg (DE)

(73) Assignee: aap Biomaterials GmbH (DE)

( * ) Notice: Subject to any disclaimer, the term of this patent is extended or adjusted under 35 U.S.C. 154(b) by 427 days.

(21) Appl. No.: 12/129,083

(22) Filed: May 29, 2008

(65) Prior Publication Data

US 2008/0304355 A1   Dec. 11, 2008

(30) Foreign Application Priority Data

Jun. 4, 2007   (DE) .......................... 10 2007 026 034

(51) Int. Cl.
*B01F 11/00*   (2006.01)
(52) U.S. Cl. ........................................................ 366/256
(58) Field of Classification Search .................. 366/256
See application file for complete search history.

(56) References Cited

U.S. PATENT DOCUMENTS

| | | | | |
|---|---|---|---|---|
| 2,855,130 | A | * | 10/1958 | Hosler ........................ 222/386.5 |
| 5,328,262 | A | | 7/1994 | Lidgren et al. |
| 5,501,520 | A | | 3/1996 | Lidgren et al. |
| 5,551,778 | A | * | 9/1996 | Hauke et al. ................... 366/139 |
| 2004/0267272 | A1 | * | 12/2004 | Henniges et al. ............... 606/93 |
| 2007/0217282 | A1 | * | 9/2007 | Lidgren et al. ................ 366/108 |

FOREIGN PATENT DOCUMENTS

| | | |
|---|---|---|
| EP | 0882436 B1 | 12/1998 |
| WO | 0185070 A1 | 11/2001 |
| WO | 2004100771 A2 | 11/2004 |
| WO | 2005122971 A1 | 12/2005 |

OTHER PUBLICATIONS

Brunold, Axel, "EP Patent Application No. 07AAP0131EPP Search Report", Sep. 17, 2008, Publisher: EPO, Published in: EP.
DIPL.-ING. Wenger, Hausruf, "German Patent Application 10 2007 026 034.4-23 Office Action", Jun. 30, 2009, Publisher: German Patent and Trademark Office, Published in: DE.

* cited by examiner

*Primary Examiner* — Walter D Griffin
*Assistant Examiner* — Christopher K VanDeusen
(74) *Attorney, Agent, or Firm* — DeMont & Breyer LLC

(57) ABSTRACT

A device for mixing and applying mixed material, in particular medical cement, comprising a cartridge cylinder, a mixer, a plunger for closing the mixed material cavity and for forcing out the mixed material from the cartridge cylinder, and a latching ring having radially outer and inner hook formations. First counter-hooks on the cartridge cylinder interact with the radially outer hook formations on the latching ring. The plunger has second counter-hooks which interact with the inner hook formation on the latching ring in order to hold the plunger during the mixing, and release the plunger for being displaced at the beginning of the application procedure.

7 Claims, 5 Drawing Sheets

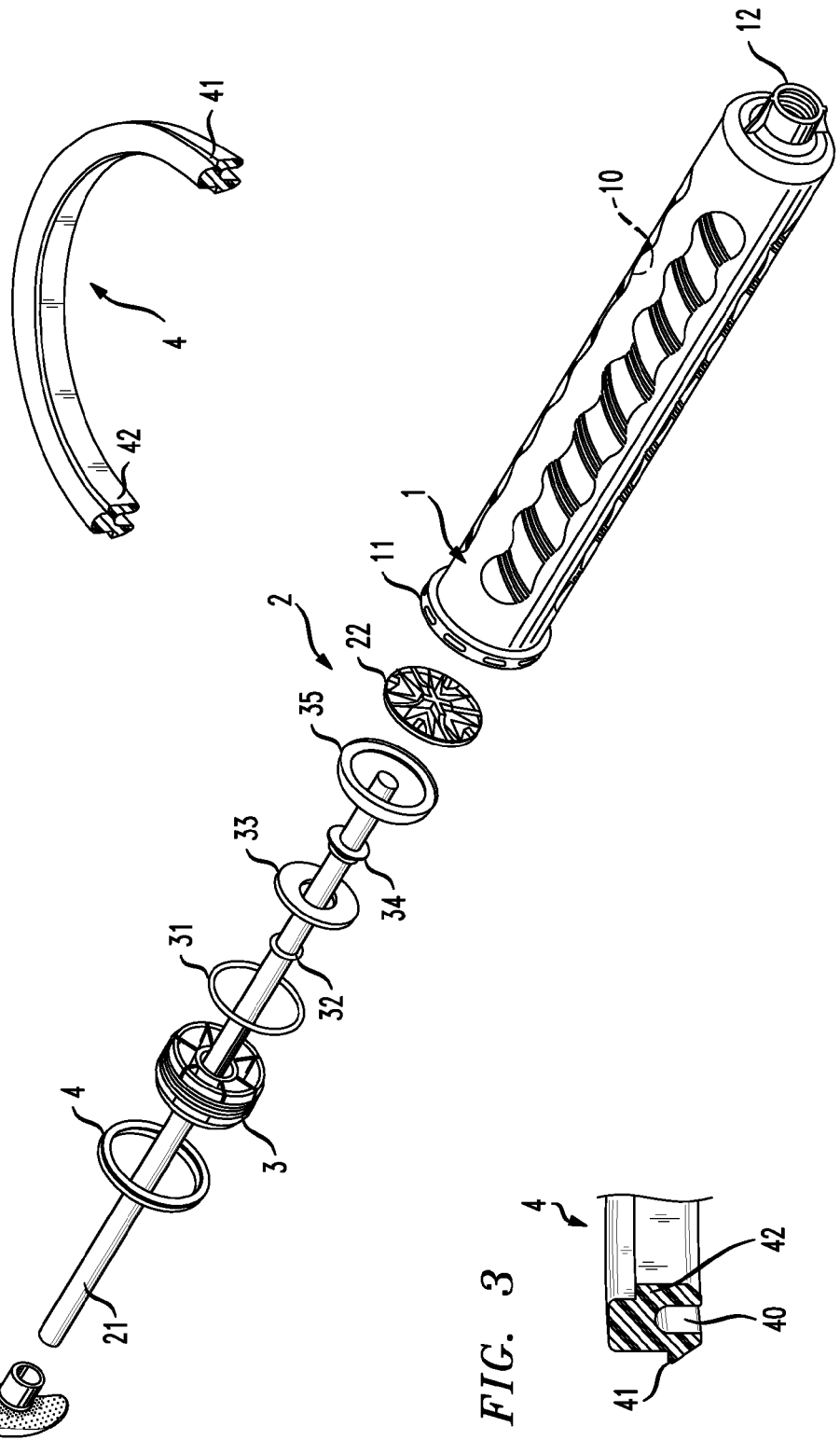

MIXING AND APPLICATION DEVICE

FIELD OF THE INVENTION

The invention relates to a device for mixing and applying mixed material, in particular medical cement, and comprises a cartridge cylinder with a mixed material cavity, a filling end and an outlet end, a mixer with an actuating rod, a mixing paddle and a grip, a plunger for closing the mixed material cavity at the filling end during the mixing and for forcing out the mixed material through the outlet end during the application, and a holding element.

BACKGROUND OF THE INVENTION

A device for mixing and applying mixed material is known from EP 1 278 488 B1. The device serves for preparing a pasty, flowable composition from a liquid component and a powdered component, which set with a time delay during mixing. In the case of medical cement, also known as bone cement, the mixing operation and the application of the medical cement must take place under sterile conditions, which leads to certain constraints on the design of the device. Even if the device is used only once and then disposed of, all the components must be easily accessible for sterilisation. For this reason, structural forms that are as simple as possible are desired. A further requirement in the case of such devices is for simple handling, in order to avoid the risk of errors.

The previously known device (EP 1 278 488 B1) has a closure cap, to lock the plunger on the filling end of the cartridge cylinder before the mixing operation is commenced. When the mixed material is to be applied, the closure cap must be removed in order to unlock the plunger. The closure cap consequently represents a holding element for temporarily fastening the plunger to the filling end, an element which has to be removed.

SUMMARY OF THE INVENTION

The invention is based on the object of simplifying a mixing and application device of the type stated at the beginning in its structural design and handling.

To achieve this object, the holding element is formed as a latching ring with radially outer and inner latching means. In order to hold the latching ring, the filling end of the cartridge cylinder has first counter-latching means, which interact with the outer latching means of the latching ring when the plunger closes the mixed material cavity. The plunger also has second counter-latching means, which interact with the inner latching means of the latching ring, in order to hold the plunger during the mixing but release it at the beginning of the application operation, so that the plunger can be pushed forwards by means of an applicator and the mixed material forced out through the outlet end of the cartridge cylinder.

The interaction of the latching ring with the filling end of the cartridge cylinder on the one hand and the plunger on the other hand is such that the plunger with the latching ring attached can be fitted manually into the filling end of the cartridge cylinder with a latching-in action, but the latching connection between the latching ring and the plunger is so strong that the plunger is not displaced into the interior of the mixed material cavity when it is manually fitted in this way. Only the applicator is capable of overcoming the holding force of the latching engagement between the latching ring and the plunger, in order then to use the plunger for forcing the mixed material out of the mixed material cavity.

The plunger has an annular receiving groove for the latching ring, which is fitted with a ring portion into this receiving groove in a snapping-in manner. For this purpose, the wall of the latching groove is formed so as to yield and has latching hooks which can resiliently yield because of the yielding nature of the wall. The yielding nature of the wall is produced by slits in the plunger wall in the region of the latching groove, the length of the slits providing the designer with a means for setting the resiliently yielding nature of the latching hooks to the correct amount. For example, the latching-holding force of the latching ring on the plunger is chosen to be stronger than the force that is required for fitting the plunger together with the latching ring onto the filling end of the cartridge cylinder. This ensures that, when the plunger together with the latching ring is fitted on the filling end of the cartridge cylinder, the plunger is not unintentionally pressed too far into the interior of the mixed material cavity.

In order to latch the plunger on the filling end of the cartridge cylinder by means of the latching ring, the filling end of the cartridge cylinder has a flanged ring, the radial extent of which is greater than the wall of the cartridge cylinder. As a result, an annular cavity with a diameter greater than that of the mixed material cavity is formed, and this annular cavity is constricted by hook-shaped projections, behind which an annular hook formation of the latching ring comes to lie when the plunger with the attached latching ring is pressed into the filling end of the cartridge cylinder.

BRIEF DESCRIPTION OF THE DRAWINGS

An exemplary embodiment of the invention is described on the basis of the drawing, in which:

FIG. 1 shows the individual parts of the mixing and application device in an exploded representation, FIG. 2 shows a latching ring, cut through, FIG. 3 shows an enlarged representation of the latching ring cross section.

DETAILED DESCRIPTION

Figure 4:
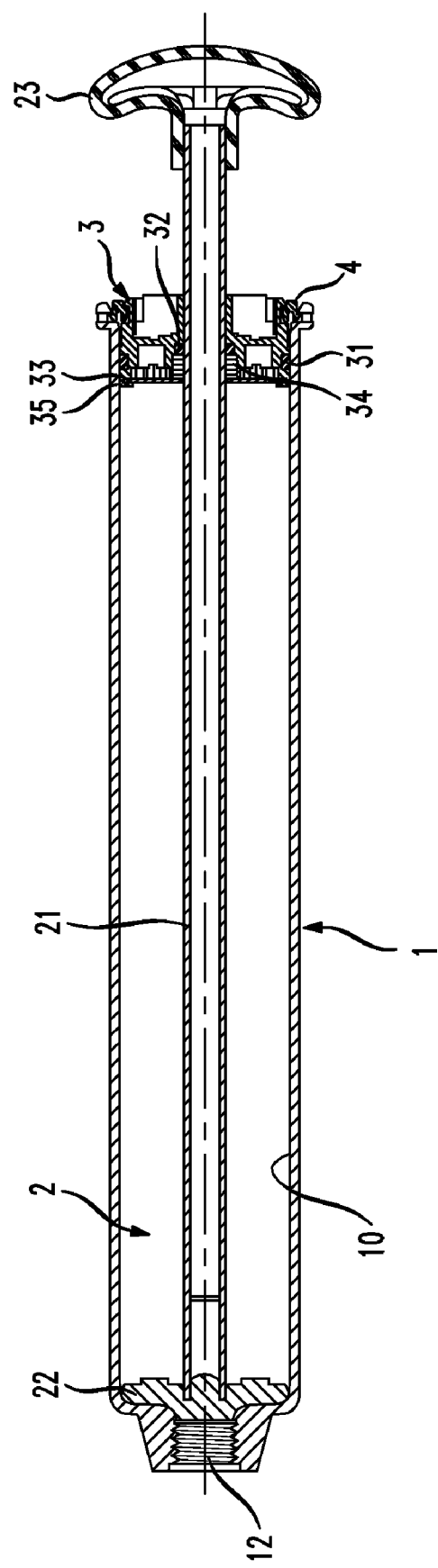
FIG. 4 shows a longitudinal section through the mixing and application device.

FIG. 1 shows the individual parts of the device and FIG. 4 shows the assembly. To be mentioned as main parts of the device are a cartridge cylinder 1, a mixture 2, a plunger 3 and a latching ring 4. The cartridge cylinder 1 has a mixed material cavity 10, a filling end 11 and an outlet end 12. Associated with the outlet end is a screw closure (not represented), also referred to as a base, which after the mixing of the mixed material is exchanged for an application tube, also referred to as a snorkel.

The mixer 2 comprises an actuating rod 21, a mixing paddle 22 at the front end and a grip 23 at the rear end. The mixing paddle 22 has sector-shaped through-openings, through which the mixed material is forced during the turning and moving back and forth of the actuating rod, and is thereby mixed.

Figure 6:
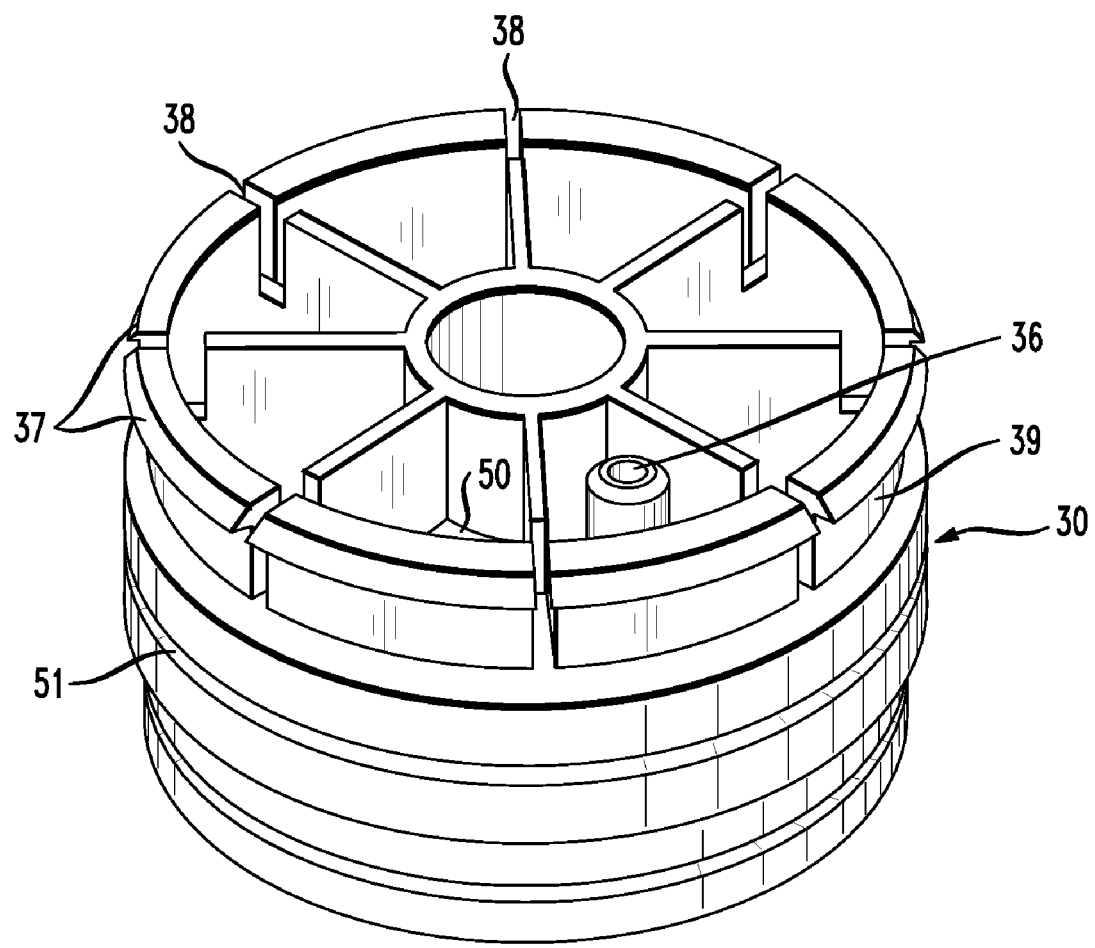
FIG. 6 shows an enlarged representation of the plunger of the device and FIG. 7 shows a further enlarged sectional representation of the engagement of the latching ring on the filling end and on the plunger of the device.

The plunger 3 comprises a plunger body 30, which can best be seen from FIG. 6, also (see FIGS. 1 and 4) a large O-ring 31 for sealing at the cavity 10, a small O-ring 32 for sealing at the actuating rod 21, a filter disk 33, a small clip ring 34 and a large clip ring 35. After placing the O-rings 31, 32 and the filter disk 33 in corresponding receiving grooves on the inner ends of the plunger body 30 (at the bottom in FIG. 6), the clip rings 34, 35 are fitted onto the plunger body 30, in order to fix and fasten the O-rings and the filter disk on the plunger. On the outer end (at the top in FIG. 6), the plunger also has a suction connection piece 36, which leads to a space inside the plunger and on which the filter disk 33 is placed. The suction connection serves the purpose of sucking troublesome air in the mixing space 10 away through the filter disk 33, while the mixed material is held back in the mixed material cavity by the filter disk 33.

The latching ring 4 serves for the temporary fastening of the plunger 3 to the filling end 11 of the cartridge cylinder 1. For this purpose, the latching ring 4 has radially outer, annular latching means 41 and radially inner, annular latching means 42, which in the cross section of the latching ring respectively appear as a hook formation 41 and as a cylindrical ring portion 42 with an insertion bevel (see FIGS. 3 and 7). The latching means 41, 42 are separated from each other by a groove 40 and thereby assume a resilient yielding nature, which is useful when fitting the latching ring.

Figure 5:
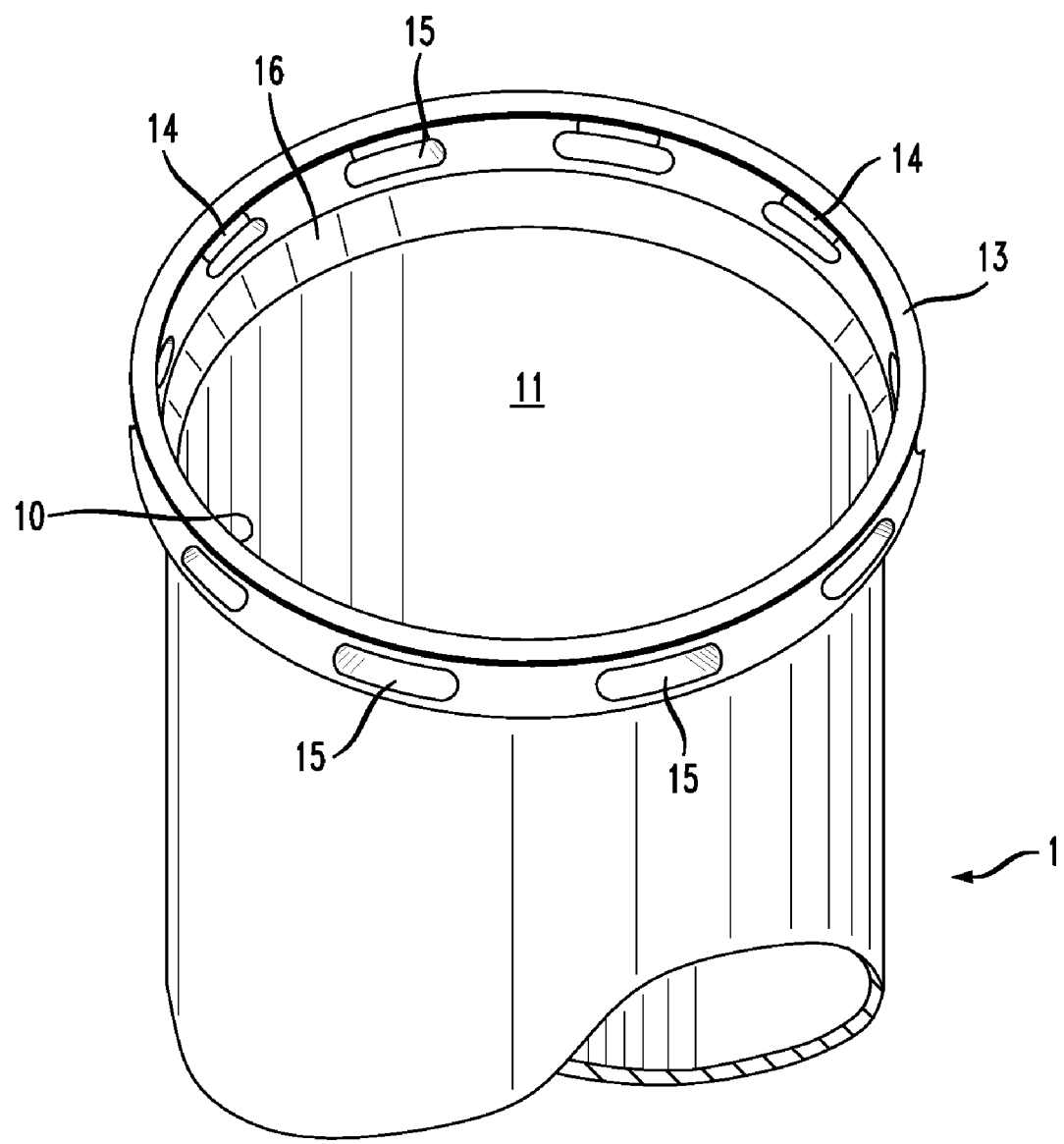
FIG. 5 shows an enlarged representation of the filling end of the device.

FIG. 5 shows a view of the filling end 11 of the cartridge cylinder 1. The latter has an edge flange 13, on the inner side of which a ring of counter-hooks 14 are located as counter-latching means for the hook formations 41 of the latching ring 4. Under the respective counter-hooks 14 there are slit-shaped slide openings 15, which are required to form the underside of the counter-hooks 14. These slits 15 open out on a placement edge 16, which forms a stop for the latching ring 4.

FIG. 6 provides a view of the outer end of the plunger body 30. The wall parts of the plunger body that are the upper wall parts in FIG. 6 are formed as resilient latching hooks 37, which are provided with insertion bevels and form the counter-latching means for the inner latching means 42 of the latching ring 4. The resiliently yielding nature of the latching hooks 37 is determined by the number and depth of axial slits 38, which subdivide the plunger wall that is the upper plunger wall in FIG. 6. Under the latching hooks 37 there is a peripheral groove 39 for receiving the latching means 42 of the latching ring 4 when the latter is coupled onto the plunger 3. The plunger body 30 also has a radial separating wall 50, through which the suction connection piece 36 reaches and which butts against the outer annular wall of the plunger in the region of a circumferential groove 51, which is formed to avoid accumulation of material. The separating wall lies outside the range of the slits 38.

Figure 7:
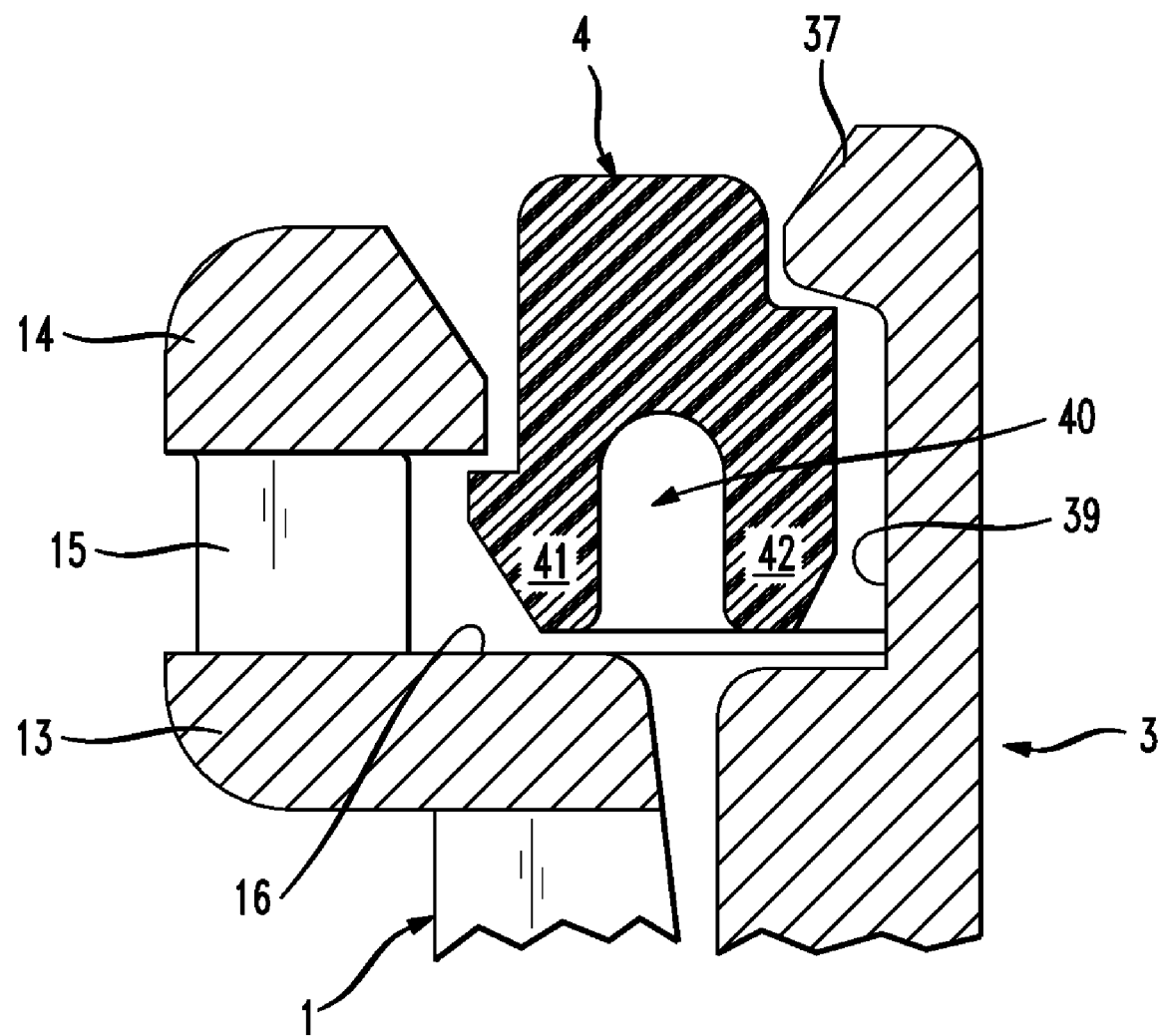

FIG. 7 shows the interaction of the latching ring 4 with the filling end 11 of the cartridge cylinder 1 and with the latching hooks 37 of the plunger 3. For fitting, the latching ring 4 is placed onto the latching hooks 37 of the plunger 3 and, by applying axially acting force to the latching ring, made to snap into the groove 39 behind the latching hooks 37. The radial extent of the cylindrical ring portion 42 determines by greater or lesser overlapping with the latching hook 37, to be chosen in the structural design, the holding force with which the latching ring 4 is held on the plunger 3. By placing the hook formations 41 of the latching ring 4 on the insertion bevel of the resilient counter-hooks 14 and pressing them axially together, the hook formations 41 snap in behind the counter-hooks 14 and hold the latching ring 4 together with the plunger 3 fitted on it on the filling end 11 of the cartridge cylinder 1. Here, too, the fitting forces can be made to match requirements by choosing the radial dimension of the hook formations 41 to be greater or smaller.

For medical applications, the mixing and application device is supplied in sterilized, ready-fitted-together structural units, namely the cartridge cylinder 1 with the attached base as a closure at the outlet end 12, the mixer 2 with the secured plunger 3 together with the placed-on latching ring 4, the components of the medical cement (bone cement) in appropriate containers, a filling funnel and an application tube (snorkel), these components being packed in a sterile form in a dish or a bag. The equipment also includes a suction pump and an applicator gun for pushing the plunger forwards and forcing the mixed material out of the cartridge cylinder.

The mixing and application device is handled as follows:

The cartridge cylinder is filled with the material to be mixed. The suction pump is connected to the suction connection piece 36, and the mixer 2 together with the plunger 3 is inserted into the filling end of the cartridge cylinder. The applied negative pressure is helpful during the fitting of the plunger 3 as a closure of the filling end, i.e. not much force has to be exerted to make the latching ring snap with its hook formation 41 in behind the resilient counter-hooks 14. By evacuating excess air and any vapors from the mixed material cavity 10, the mixed material is prepared for mixing. The mixing is performed by turning and pushing back and forth the mixing paddle 22 inside the mixed material cavity. After intimate mixing, the mixing paddle is brought to bear against the inner side of the plunger and the actuating rod 21 is broken off in such a way that the mixed material cavity remains closed. Then the cartridge cylinder can be placed onto the applicator gun, the closure base is removed and the applicator tube is instead screwed onto the outlet end. If appropriate, the applicator tube is shortened. Then the applicator gun can be actuated, pressure being exerted on the plunger 3 and tension exerted on the flange 13 of the cartridge cylinder. As a result, the holding force of the latching ring 4, with which the plunger 3 is held on the filling end 11 of the cartridge cylinder, is overcome. The plunger 3 together with the broken-off end of the actuating rod 21 inserted in it can then be displaced by the applicator gun in the direction of the outlet end 12 of the cartridge cylinder, in order to bring the mixed material to a suitable location through the applicator tube.

It is consequently evident that the novel mixing and application device has with the latching ring 4 a holding element for temporarily fastening the plunger to the filling end that need not be unlocked before attaching the applicator gun. This dispenses with the need for a locking bar that is otherwise required in the prior art (EP 1 278 488 B1) and with the need for the operation of actuating and removing the locking bar.

The invention claimed is:

1. A device for mixing material and applying the mixed material by an applicator, comprising:

a cartridge cylinder having a mixed material cavity, a filling end and an outlet end, wherein the filling end and the outlet end are located at different ends of the cartridge cylinder;

a mixer having an actuating rod, a mixing paddle and a grip;

a plunger for closing the mixed material cavity at the filling end during the mixing and for forcing out the mixed material through the outlet end by the applicator; and a latching ring having radially outer and inner hook formations for temporarily fastening the plunger to the interior of the filling end;

the filling end of the cartridge cylinder including first counter-hook formations on the interior of the filling end, which interact with the outer hook formations of the latching ring when the plunger closes the mixed material cavity; and the plunger including second counter-hook formations, which interact with the inner hook formations of the latching ring, in order to hold the plunger during mixing, and by application of a predetermined force release the plunger by unlatching the second counter-hook formations from the inner hook formations so that the plunger can be displaced by the applicator.

2. The device as claimed in claim 1, wherein said latching ring comprises a ring portion with said hook formations in cross section, and wherein said first counter-hook formations are formed as a flanged ring of the cartridge cylinder and are formed with insertion bevels to facilitate mounting of the latching ring.

3. The device as claimed in claim 2, wherein said flanged ring is arranged on the filling end of the cartridge cylinder and is provided on its inner side with said first counter-hook formations, and adjacent to the mixed material cavity, with a seat for the latching ring.

4. The device as claimed in claim 3, wherein radially-extending slit openings in the flanged ring are disposed adjacent to said first counter-hook formations.

5. The device as claimed in claim 1, wherein said inner hook formations of the latching ring are formed by a cylindrical ring portion with an insertion bevel and are separated from said outer hook formations by a groove in the latching ring, and wherein said second counter-hook formations of the plunger form resilient latching hooks provided with insertion bevels and for the latching ring, are formed from wall portions of the plunger and define an annular recess for receiving said cylindrical ring portion of the latching ring.

6. The device as claimed in claim 5, wherein said resilient latching hooks are separated from one another by axial slits in the outer wall of the plunger, the number and length of the slits being chosen with a view to the desired resilient characteristic of the latching hooks.

7. The device as claimed in claim 6, wherein the plunger comprises a radial separating wall which is located at a greater distance from the latching hooks than it corresponds to the length of the axial slits, and wherein the plunger, in the plane of its separating wall, comprises a groove on its outer circumference to avoid accumulation of material.

* * * * *